United States Patent
Matsumoto et al.

[11] Patent Number: 5,951,914
[45] Date of Patent: Sep. 14, 1999

[54] RACEMIC COMPOUND AND ANTI-FERROELECTRIC LIQUID CRYSTAL COMPOSITION

[75] Inventors: Takahiro Matsumoto; Hiroshi Mineta; Tomoyuki Yui; Masahiro Johno, all of Tsukuba, Japan

[73] Assignee: Mitsubishi Gas Chemical Company, Inc., Tokyo, Japan

[21] Appl. No.: 08/923,287

[22] Filed: Sep. 4, 1997

[30] Foreign Application Priority Data

Sep. 12, 1996 [JP] Japan ................................. 8-241921
Jan. 27, 1997 [JP] Japan ................................. 9-012521
Jan. 27, 1997 [JP] Japan ................................. 9-012522

[51] Int. Cl.$^6$ ..................... C09K 19/20; C09K 19/12
[52] U.S. Cl. ........................ 252/299.67; 252/299.64; 252/299.65; 252/299.66
[58] Field of Search .................. 252/299.67, 299.01, 252/299.64, 299.65, 299.66

[56] References Cited

U.S. PATENT DOCUMENTS 5,660,762 8/1997 Ito et al. ............................. 252/299.67

FOREIGN PATENT DOCUMENTS

| 0718274 | 6/1996 | European Pat. Off. . |
| 718274 | 6/1996 | European Pat. Off. . |
| 737733 | 10/1996 | European Pat. Off. . |
| 8-113553 | 5/1996 | Japan . |
| 8-268970 | 10/1996 | Japan . |

OTHER PUBLICATIONS

Chandani, et al., "Tristable Switching in Surface Stabilized Ferroelectric Liquid Crystals with a Large Spontaneous Polarization", Jap. Journal of Appl'd Phys., vol. 27, No. 5, May, 1988, pp. L729–L732.

Chandani, et al., "Novel Phases Exhibiting Tristable Switching", Jap. Journal of Appl. Phys., vol. 28, No. 7, Jul. 1989, pp. L1261–L1264.

Chandani, et al., "Antiferroelectric Chiral Smectic Phases Responsible for the Tristable Switching in MHPOBC", Jap. Journal of Appl. Phys., vol. 28, No. 7, Jul., 1989, pp. L1265–L1268.

Johno, et al., "Smectic Layer Switching by an Electric Field in Ferroelectric Liquid Crystal Cells", Jap. Journal of Appl. Phys., vol. 28, No. 1, Jan., 1989, pp. L119–L120.

Johno, et al., "Correspondence between Smectic Layer Switching and DC Hysteresis of Apparent Tilt Angle in an Antiferroelectric Liquid Crystal Mixture",Jap. Jrnl. of Appl. Phys., vol. 29, No. 1, Jan.,1990 pp. L111–L114.

Yamamoto, et al., "Full–Color Antiferroelectric Liquid Crystal Dislay", Preprints of the 4th International Conference on Ferroelectric Liquid Crystals, 1993, pp. 77–78.

Primary Examiner—Shean C. Wu
Attorney, Agent, or Firm—Sherman and Shalloway

[57] ABSTRACT

A racemic compound of the formula (1)

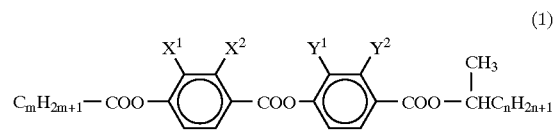

and an anti-ferroelectric liquid crystal composition consisting essentially of said racemic compound and one anti-ferroelectric liquid crystal compound of the formula (2) or a mixture of two or more compounds selected from anti-ferroelectric liquid crystal compounds of the formula (2),

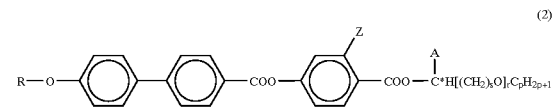

said composition having excellent steepness of threshold, having an anti-ferroelectric phase in a broad temperature range and having the performance of a high response speed and a high contrast.

11 Claims, 3 Drawing Sheets

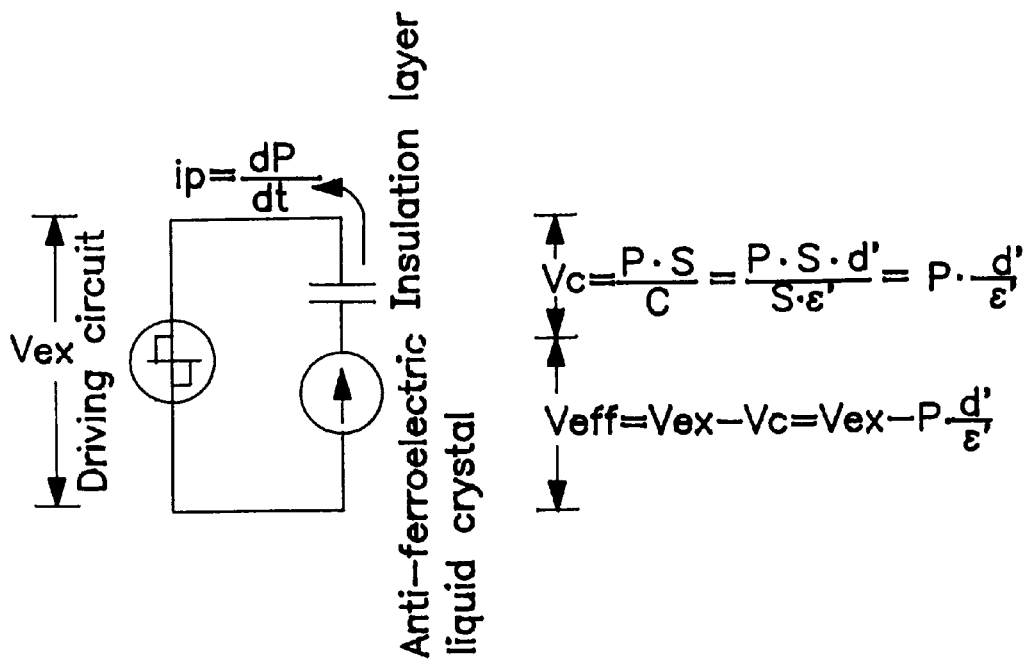

Vex: Drive voltage applied to device

Vc: Voltage generated between the upper and lower surfaces of an alignment layer by the charge of a polarization inversion current Veff: Effective voltage actually applied to liquid crystal P: Polarization of liquid crystal Ip: Polarization inversion current S: Electrode area of liquid crystal device d': Thickness of alignment layer ε': Dielectric constant of alignment layer

FIG. 1

RACEMIC COMPOUND AND ANTI-FERROELECTRIC LIQUID CRYSTAL COMPOSITION

FIELD OF THE INVENTION

The present invention relates to a novel racemic compound, a novel anti-ferroelectric liquid crystal composition containing the same and a liquid crystal display device for which the composition is used.

PRIOR ART

A liquid crystal display device has been so far developing as an attractive display device due to its low voltage operation, low power consumption and display capability with a thin screen. Further, a liquid crystal display device is recently practically being applied to the fields of information and office automation-related machines and equipment and the field of television sets and at the same time, it is being applied to various fields of other use. Under the circumstances, energetic developments are under way for obtaining a liquid crystal display device having a display capacity and a display quality over a conventional CRT display device.

Liquid crystals used in presently available liquid crystal display devices are nematic liquid crystals, and they are classified into simple matrix driven liquid crystals and active matrix driven liquid crystals on the basis of driving methods.

Simple matrix driven liquid crystal display devices are produced advantageously in view of a cost due to their simple structures. However, the problems of these devices are that the contrast is low due to a cross-talk phenomenon, that driving in a large capacity is difficult and that the display of video frame rate is difficult due to a low response speed. It is therefore necessary to break through many technical problems for attaining a large-sized liquid crystal display device capable of displaying video frame rate.

On the other hand, active matrix driven liquid crystal display devices use a TFT (thin film transistor) method as a main stream, while it is required to form thin film transistors for each of pixels, and a large investment is required for high production technology and the construction of a production line. The active matrix driving is therefore far disadvantageous in view of a cost as compared with the simple matrix driving. However, the active matrix driven liquid crystal display device has a high contrast since the cross-talk phenomenon which is a problem of the simple matrix driving method is few, and further, its response speed is high. There can be therefore attained a liquid crystal display device which has a high image quality and is capable of displaying video frame rate. For this reason, the TFT method among the active matrix driving methods is gaining its position as a main stream.

At present, however, large-sized liquid crystal devices having a size of 10 to 20 inches are being developed, and the problem as for viewing angle dependency inevitable to a device using a nematic liquid crystal becomes critical.

Various technical studies have been made for overcoming the viewing angle dependency and as a result, displaying with a viewing angle of about 140° has been possible without a gray scale inversion. However, the contrast is still greatly dependent upon a viewing angle, and at present, there can not be obtained such flat contrast characteristics as achieved in CRT with an extent of the wide viewing angle.

Under the circumstances, a liquid crystal display device for which a ferroelectric liquid crystal is used is attracting attention as a fast response liquid crystal display device. A surface stabilized ferroelectric liquid crystal (SSFLC) device disclosed by Clark and Lagerwall attracts attention in that it has a fast response speed and a wide viewing angle which have not been achieved in the past. Its switching characteristics have been studied in detail, and a number of ferroelectric liquid crystal compounds have been synthesized for optimizing various physical property constants.

For accomplishing a practical device, there have been a number of technical barriers to be overcome such as difficulties in achieving a memory effect and controlling a layer structure due to a difficulty in controlling an alignment, the destruction of an alignment caused by a mechanical shock, and the like, and these problems have been overcome to produce a device as a product. However, the ferroelectric liquid crystal display device still has problems that color display is not possible since gray scale is impossible in principle and that high speed response has not been attained so that video frame rate display is difficult to obtain.

Further, as another fast response liquid crystal display device, the development of a device having a switching mechanism different from that of SSFLC is also under way. It is a liquid crystal display device which uses switching among tristable states of a liquid crystal compound having an anti-ferroelectric phase (to be referred to as "anti-ferroelectric liquid crystal compound" hereinafter) (Japanese Journal of Applied Physics, Vol. 27, pp. L729, 1988).

An anti-ferroelectric liquid crystal device has three stable states, i.e., two uniform states (Ur, Ul) observed in a ferroelectric device and a third state. Chandani et al report that the above third state is an anti-ferroelectric phase (Japanese Journal of Applied Physics, vol. 28, pp. L1261 (1989) and Japanese Journal of Applied Physics, vol. 28, pp. L1265 (1989)). The above switching among tristable states is the first characteristic of an anti-ferroelectric liquid crystal device. The second characteristic of the anti-ferroelectric liquid crystal device is that a sharp threshold is present with regard to an applied voltage. Further, it has a memory effect when a proper bias voltage is set, which is the third characteristic of the anti-ferroelectric liquid crystal device.

Further, the fourth characteristic feature of the anti-ferroelectric liquid crystal is that its layer structure easily is switched when an electric field is applied (Japanese Journal of Applied Physics, Vol. 28, pp. L119 (1989) and Japanese Journal of Applied Physics, vol. 29, pp. L111 (1990)). Owing to this characteristic, a liquid crystal display device free of defects and having self-restoring ability of the alignment can be produced.

By utilizing the above characteristics, a liquid crystal device having a high response speed and an excellent contrast can be achieved.

Further, it has been demonstrated that the gray scale, which is almost impossible with a ferroelectric liquid crystal device, is possible with an anti-ferroelectric liquid crystal device. It has been consequently made possible to shift toward a full-color display, and the importance of an anti-ferroelectric liquid crystal is increasing (Preprints of No. 4 Ferroelectric Liquid Crystal International Symposium, page 77, (1993)).

Under the circumstances, energetic developments are under way for achieving an anti-ferroelectric liquid crystal display device, but the developments are presently encountering the following problems.

When an anti-ferroelectric liquid crystal is used in a display device, generally, the anti-ferroelectric liquid crystal is sandwiched between two glass substrates provided with an insulation layer and an alignment layer. The insulation layer is used for preventing a short circuit, and it is required to have a certain thickness for the complete prevention of a short circuit. On the other hand, the alignment layer is required for aligning liquid crystal molecules in a certain direction, and it is also required to have a certain thickness for decreasing alignment defects in number as small as possible, which defects are caused when the liquid crystal molecules are aligned.

When a voltage is applied to a liquid crystal display device formed as described above, and when the insulation layer and the alignment layer have a small thickness or when they are absent, the phase transition from an anti-ferroelectric state to a ferroelectric state sharply occurs with regard to the applied voltage. However, when the insulation layer and the alignment layer have a thickness required for practical use, the phase transition from an anti-ferroelectric state to a ferroelectric state takes place gradually with regard to the applied voltage.

In the driving of an anti-ferroelectric liquid crystal, a holding voltage lower than a writing voltage is continuously applied for a predetermined period of time after the writing voltage is applied, for producing a memory effect. When the phase transition from an anti-ferroelectric state to a ferroelectric state takes place moderately with regard to a charged voltage as described above, that is, in a liquid crystal display device having a low steepness of threshold, the holding voltage that can be selected is limited to a very narrow range, and in an extreme case, the holding voltage cannot be set, and no memory effect is secured. This means that an anti-ferroelectric liquid crystal display device is no longer used as such, which is a serious problem.

Further, in the device with a low steepness of threshold, the breadth of the holding voltage that can be selected decreases, and a so-called driving margin decreases. A practical device is therefore required to have a high steepness of threshold, and liquid crystal materials which can give such a steepness of threshold are therefore being demanded.

As described above, practically, it is preferred that an anti-ferroelectric liquid crystal should have the property of giving a high steepness of threshold when used in a liquid crystal display device.

It has been also experimentally shown that the steepness of threshold of a liquid crystal display device considerably has a relationship with the thickness of each of the insulation layer and the alignment layer.

It has been studied what factors can explain the above relationship. In the following studies, both an insulation layer and an alignment layer will be together referred to as an "alignment layer".

For facilitating the understanding of the studies, the studies will be explained with reference to FIGS. 1 to 5 below.

BRIEF DESCRIPTION OF DRAWINGS

FIG. 1 shows an equivalent circuit of an anti-ferroelectric liquid crystal device.

FIG. 1 shows an equivalent circuit which comprises an electric current source to generate a polarization current according to an applied voltage, an alignment layer that is an electrostatic capacitor (C) to connect with an anti-ferroelectric liquid crystal in series, and a driving circuit that is an ideal voltage source.

In FIG. 1, the drive voltage applied to a device is taken as Vex, a voltage generated between the upper and lower surfaces of an alignment layer by the charge of a polarization inversion current is taken as Vc, an effective voltage to be actually applied to the liquid crystal is taken as Veff, a spontaneous polarization of the liquid crystal is taken as P, an electrode area of the liquid crystal device is taken as S, a thickness of the alignment layer is taken as d', and a dielectric constant of the alignment layer is taken as $\epsilon'$.

Vc is calculated as follows.

$$Vc=PS/C=PSD'/(S\epsilon)=P(d'/\epsilon') \tag{1}$$

On the basis of the above equation, Veff is expressed by the following equation.

$$Veff=Vex-Vc=Vex-P(d'/\epsilon') \tag{2}$$

As shown in the equation (2), the voltage actually applied to the liquid crystal is lower than the externally applied voltage by a product of the polarization P of the liquid crystal, the thickness d' of the alignment layer and a reciprocal number $1/\epsilon'$ of the dielectric constant of the alignment layer.

Then, when a thickness of the liquid crystal filled in a liquid crystal cell is taken as d, an electric field Eeff actually applied to the liquid crystal is expressed by the following equation.

$$Eeff=Veff/d \tag{3}$$

On the other hand, an apparent electric field strength Eex is expressed by the following equation (4)

$$Eex=Vex/d=(Veff+Vc)/d=Veff/d+P(d'/\epsilon')/d=Eeff+\alpha \tag{4}$$

in which $$\alpha=d'/(\epsilon'd) \tag{5}$$

When no alignment layer is present, the second term in the equation (4) is 0, and then Eex=Eeff.

Figure 2:
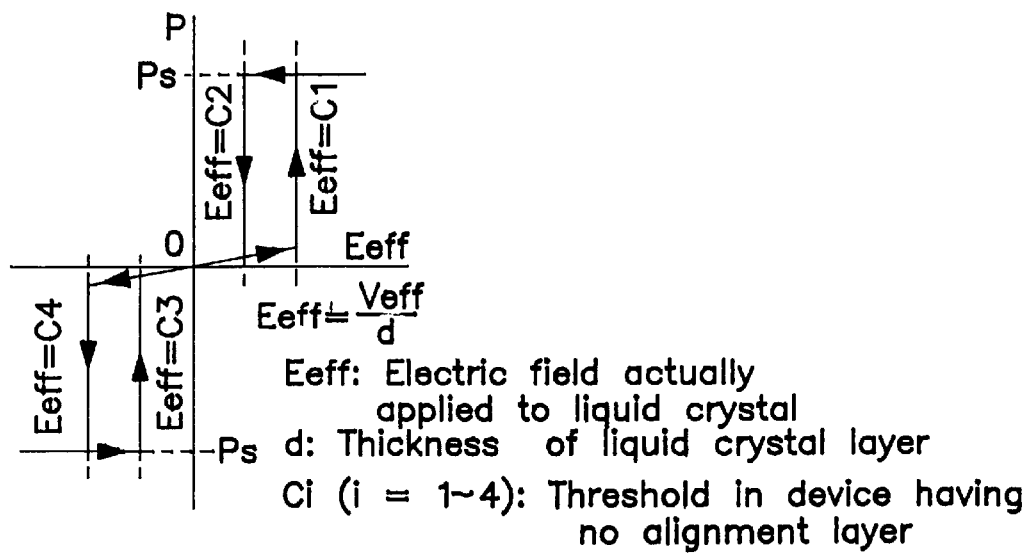
FIG. 2 shows a simulation result on the steepness of threshold when no alignment layer is present.

An anti-ferroelectric liquid crystal shows a hysteresis of its optical response with regard to an applied voltage, while four thresholds are thinkable with regard to the hysteresis. Each threshold is Eeff (=Eex), and in this case, these thresholds do not incline with regard to an electric field. FIG. 2 shows this appearance.

When an alignment layer is present, the equation (4) is modified to obtain the following equation.

$$Eeff=Eex-\alpha P \tag{6}$$

Figure 3:
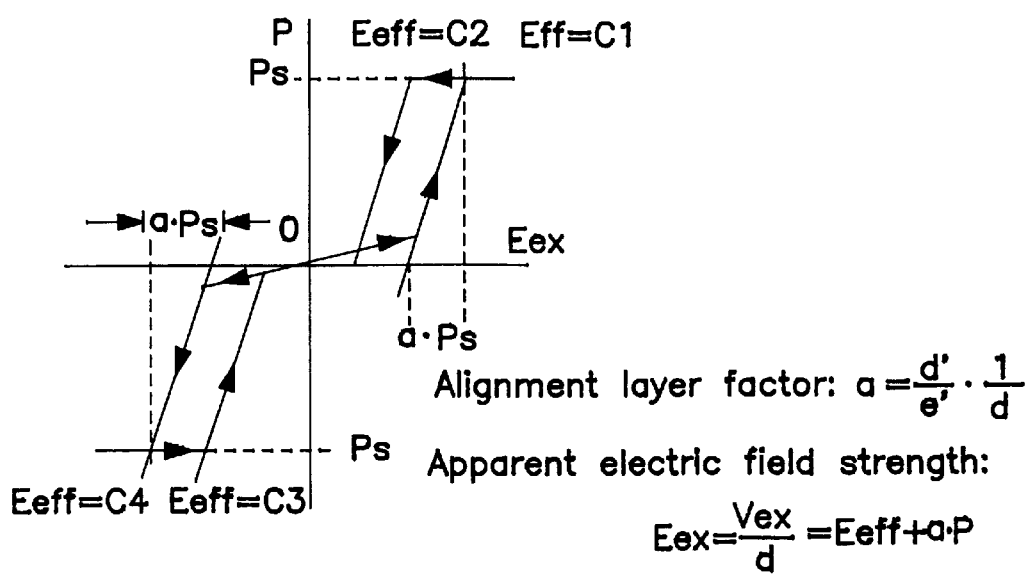
FIG. 3 shows a simulation result on the steepness of threshold when an alignment layer is present.

That is, an effective electric field exerting on the liquid crystal is lower than the applied electric field Eex by $\alpha \cdot P$. As a result, the hysteresis is strained to a great extent due to the contribution of the $\alpha \cdot P$ as shown in FIG. 3.

The above studies show that the strain of hysteresis is greatly caused by mutual effects of the spontaneous polarization and the alignment layer. For obtaining a liquid crystal device having a reduced strain of hysteresis, it is required to decrease the above mutual effects to a level as low as possible.

For the above purpose, the measures that can be specifically taken include the use of an alignment layer having a high dielectric constant, decreasing of thickness of the alignment layer and decreasing of spontaneous polarization of the liquid crystal, as is clear from the above equations (5) and (6). In the above measures, there are not many kinds of compounds having a high dielectric constant that can be industrially used, and it is therefore difficult to select a usable alignment layer.

It is eventually specific measures to decrease the thickness of the alignment layer and decrease the spontaneous polarization of the liquid crystal.

Generally, an anti-ferroelectric liquid crystal compound has a considerably large spontaneous polarization, and a liquid crystal compound having relatively excellent physical properties has a spontaneous polarization of 200 nC/cm$^2$ or more. Therefore, if the thickness of the alignment layer is not much decreased, the strain of the hysteresis is considerably large. However, when the thickness of the alignment layer is decreased, there occurs a problem that the alignment state of the liquid crystal molecules is too defective to secure a contrast. The measure of decreasing the thickness of the alignment layer for correcting the strain of the hysteresis is therefore considerably limited.

On the other hand, the spontaneous polarization of a liquid crystal compound is decreased by a method in which a proper compound having no spontaneous polarization is mixed with the liquid crystal compound, that is, the liquid crystal compound is diluted in concentration. Since, however, the response speed of a liquid crystal is determined by a product of an applied voltage and a spontaneous polarization, there is another new problem that the response speed decreases when the spontaneous polarization is simply decreased by dilution.

For obtaining a device having a decreased strain of hysteresis, attempts have been so far made to develop an anti-ferroelectric liquid crystal compound having a low spontaneous polarization, a low threshold voltage and a low viscosity, while no satisfactory achievements have been obtained.

The present invention has been made from the points of view described above, and has been completed by finding the following. By the selection and addition of a racemic compound having a proper chemical structure as means of decreasing the spontaneous polarization for decreasing the strain of hysteresis of an anti-ferroelectric liquid crystal compound, the spontaneous polarization can be decreased without decreasing the response speed, and when a composition containing the above racemic compound is used for forming a liquid crystal device, the liquid crystal device shows a decreased strain of hysteresis.

That is, according to the present invention, there is provided a racemic compound of the following formula (1),

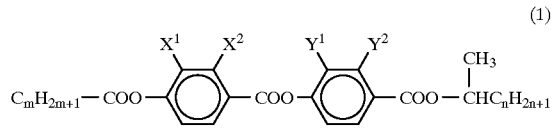

(1)

wherein m is an integer of 3 to 12, n is an integer of 3 to 8, each of $X^1$ and $X^2$ is a hydrogen atom together or one is a hydrogen atom and the other is a fluorine atom, and each of $Y^1$ and $Y^2$ is a hydrogen atom together or one is a hydrogen atom and the other is a fluorine atom.

According to the present invention, further, there is provided an anti-ferroelectric liquid crystal composition consisting essentially of the racemic compound of the above formula (1) and an anti-ferroelectric liquid crystal compound of the following formula (2),

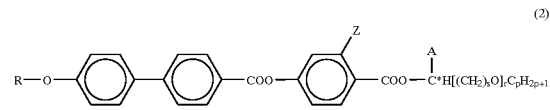

(2)

wherein R is a linear alkyl group having 6 to 12 carbon atoms, Z is a hydrogen atom or a fluorine atom, A is —CH$_3$ or —CF$_3$, and r is 0 or 1, provided that when A is —CH$_3$, r is 0 and p is an integer of 4 to 10, that when A is —CF$_3$ and r is 0, p is an integer of 6 to 8, and that when A is —CF$_3$ and r is 1, s is an integer of 5 to 8 and p is an integer of 2 or 4.

The present invention will be more specifically explained hereinafter.

The racemic compound of the above formula (1) is preferably a compound of the formula (1) in which m is an integer of 3 to 6, particularly preferably a compound of the formula (1) in which m is 9 and n is 6. Further, the racemic compound of the formula (1) is preferably a compound of the formula (1) in which each of $X^1$, $X^2$ and $Y^2$ is a hydrogen atom together and $Y^2$ is a fluorine atom.

The racemic compound of the formula (1) can be easily produced by the following method.

(a) HO—Ph(X)—COOH+RCOCl→RCOO—Ph(X)—COOH
(b) (a)+SOCl$_2$→RCOO—Ph(X)—COCl
(c) AcO—Ph(Y)—COOH+SOCl$_2$→AcO—Ph(Y)—COCl
(d) (c)+R'(OH)→AcO—Ph(Y)—COOR'
(e) (d)+(Ph—CH$_2$NH$_2$)→HO—Ph(Y)—COOR'
(f) (b)+(e)→end product In the above formulae, AcO— is an acetyl group, each of —Ph(X)— and —Ph(Y)— is a 1,4-phenylene group in which a fluorine atom may be substituted, R is a linear alkyl group, R' is a racemic alcohol moiety, and Ph— is a phenyl group.

The above production method will be briefly explained below.

(a) shows a reaction between fluorine-substituted or non-substituted p-hydroxybenzoic acid and alkylcarboxylic acid chloride to form an ester.

(b) shows the chlorination of the ester obtained in (a).

(c) shows the chlorination of fluorine-substituted or non-substituted p-acetoxybenzoic acid with thionyl chloride.

(d) shows a reaction between a chlorination product obtained in (c) and a racemic alcohol to form an ester.

(e) shows the deacetylation of the ester obtained in (d).

(f) shows the formation of a racemic compound by a reaction between a chlorination product obtained in (b) and a phenol obtained in (e).

The anti-ferroelectric liquid crystal composition of the present invention consists essentially of the racemic compound of the above formula (1) and the anti-ferroelectric liquid crystal compound of the above formula (2). The compound of the formula (2) is particularly preferably a compound of the formula (2) in which (i) A is —CF$_3$, r is 1, s is an integer of 5 to 8 and p is 2 or 4, or in which (ii) A is —$CH_3$, r is 0 and p is an integer of 4 to 6, since a composition containing the above compound is well-balanced in various physical properties.

The anti-ferroelectric liquid crystal compound of the formula (2) used in the present invention can be easily produced as shown in the following method. For example, a compound of the formula (2) in which A=$CF_3$, p=2, r=1 and s=5 is produced by the following method.

(a) AcO—Ph(Z)—COOH+$SOCl_2$→AcO—Ph(Z)—COCl (b) (a)+HOC*H($CF_3$)($CH_2$)$_5$O$C_2H_5$→AcO—Ph(Z)—COOC*H($CF_3$)($CH_2$)$_5$O$C_2H_5$ (c) (b)+Ph—$CH_2NH_2$→HO—Ph(Z)—COOC*H($CF_3$)($CH_2$)$_5$O$C_2H_5$ (d) RO—Ph—Ph—COOH+$SOCl_2$→RO—Ph—Ph—COCl (e) (b)+(d)→anti-ferroelectric liquid crystal compound In the above formulae, AcO— is an acetyl group, —Ph(Z) is a 1,4-phenylene group in which fluorine may be substituted, Ph— is a phenyl group, —Ph— is a 1,4-phenylene group and C* is an asymmetric carbon atom.

The above production method will be briefly explained below.

(a) shows the chlorination of fluorine-substituted or non-substituted p-acetoxybenzoic acid with thionyl chloride.

(b) shows a reaction between a chlorination product obtained in (a) and an alcohol to form an ester.

(c) shows the deacetylation of the ester obtained in (b).

(d) shows the chlorination of alkyloxybiphenylcarboxylic acid.

(e) shows the formation of a liquid crystal by a reaction between a phenol obtained in (c) and a chlorination product obtained in (d).

The anti-ferroelectric liquid crystal composition of the present invention consists essentially of the racemic compound of the formula (1) and the anti-ferroelectric liquid crystal compound of the formula (2). Specifically, it is advantageous that the total amount of the compounds of the formulae (1) and (2) based on the total composition is at least 70 mol %, preferably at least 80%.

The compound of the formula (1): the compound of the formula (2) mixing ratio is preferably in the range of 1:99 to 60:40, particularly preferably 5:95 to 50:50, in terms of a molar ratio.

Further, the following has been also found in the present invention. One compound or a mixture of at least two compounds of the formula (2) may used, while it is preferred to use a mixture of at least two compounds of the formula (2) as the compound of the formula (2), and it is particularly preferred to use a mixture of a compound of the formula (2) in which (i) A is —$CF_3$, r is 1, s is an integer of 5 to 8 and p is 2 or 4 and a compound of the formula (2) in which (ii) A is —$CH_3$, r is 0 and p is an integer of 4 to 6, since there can be obtained a liquid crystal display device which is excellent in alignment characteristic and steepness of threshold and exhibits a high contrast.

It is practically preferable that anti-ferroelectric liquid crystal composition of the present invention has at least a smectic A phase and has an anti-ferroelectric phase in a temperature range of from 0 to 40° C. The anti-ferroelectric liquid crystal composition of the present invention is preferably used in an anti-ferroelectric liquid crystal display device using the composition interposed between a pair of electrode substrates.

The present invention provides a novel recemic compound and a novel anti-ferroelectric liquid crystal composition. The anti-ferroelectric liquid crystal composition of the present invention provides an anti-ferroelectric liquid crystal display device which is excellent in steepness of threshold, has an anti-ferroelectric phase in a broad temperature range, exhibits a high response speed, and which therefore has a high display quality and a high contrast.

EXAMPLES

The present invention will be explained with reference to Examples hereinafter, while the present invention shall not be limited thereto.

Example 1

Preparation of 4-(1-methylheptyloxycarbonyl) phenyl=4-decanonyloxybenzoate (formula (1): m=9, $X^1=X^2=Y^1=Y^2$=H, n=6 (E1)

(1) Preparation of 4-decanonyloxybenzoic acid 12.7 Grams (0.0917 mol) of p-hydroxybenzoic acid was added to 150 ml (milliliter) of dichloromethane, and to the resultant suspension was added 10.2 g (0.0917 mol) of triethylamine. The mixture was stirred to form a uniform solution. To the above solution was added 18.3 g (0.096 mol) of decanoyl chloride at such an appropriate rate at which dichloromethane was not refluxed. Then, 1.0 g (0.0085 mol) of 4-dimethylaminopyridine was added, and the mixture was stirred at room temperature overnight. 1N hydrochloric acid was added to the resultant reaction mixture, and the mixture was extracted with ether. The ether was distilled off, and the resultant crude product was washed with hexane and dried to give 19.4 g (yield 85%) of an intended carboxylic acid as an end product.

(2) Preparation of 4-acetoxy-1-(1-methylheptyloxycarbonyl)benzene

Thionyl chloride in an amount of 60 ml was added to 10.8 g (0.06 mol) of 4-acetoxybenzoic acid, and the mixture was allowed to react under reflux for 7 hours. Then, excessive thionyl chloride was distilled off, and then 10 ml of pyridine and 5.24 g (0.0402 mol) of 1,2-octanol were dropwise added. After the dropwise addition, the mixture was stirred at room temperature for one day and night, and then the reaction mixture was diluted with 200 ml of ether. An organic layer was consecutively washed with a diluted hydrochloric acid, with a 1N sodium hydroxide aqueous solution and with water, and dried over magnesium sulfate. The solvent was distilled off, and the resultant crude end product was purified by silica gel column chromatography using hexane/ethyl acetate as solvents to give 10.6 g (yield 90%) of an end product.

(3) Preparation of 4-hydroxy-1-(1-methylheptyloxycarbonyl)benzene 10.6 Grams (0.0361 mol) of the compound obtained in the above (2) was dissolved in 250 ml of ethanol, and 7.74 g (0.0772 mol) of benzylamine was dropwise added. The mixture was stirred at room temperature for one day and night, then diluted with 300 ml of ether, consecutively washed with diluted hydrochloric acid and with water, and dried over magnesium sulfate. The solvent was distilled off, and then silica gel column chromatography was used for isolation and purification to give 8.9 g (yield 98%) of an end product.

(4) Preparation of 4-(1-methylheptyloxycarbonyl)phenyl=4-n-decanoyloxybenzoate

Thionyl chloride in an amount of 15 ml was added to 3.1 mmol of the compound obtained in the above (3), and the mixture was refluxed under heating for 5 hours. Excessive thionyl chloride was distilled off, then, 2 ml of pyridine and 2.12 mmol of the compound obtained in the above (3) were added, and the mixture was allowed to react at room temperature for 10 hours.

After termination of the reaction, the reaction mixture was diluted with 300 ml of ether and consecutively washed with diluted hydrochloric acid, with a 1N sodium carbonate aqueous solution and with water, and an organic layer was dried over magnesium sulfate. Then, the solvent was distilled off, and silica gel column chromatography was used for isolation and purification to give 0.96 g (yield 87%) of an end product.

Examples 2–7

Preparation of 3-fluoro-4-(1-methylheptyloxycarbonyl)phenyl=4-decanoyloxybenzoate (formula (1); m=9, $X^1=X^2=Y^1=H$, $Y^2=F$, n 6 (E2)), 4-(1-methylheptyloxycarbonyl)phenyl=2-fluoro-4-decanoyloxybenzoate (formula (1): m=9, $X^1=Y^2=Y^1=H$, $X^2=F$, n=6 (E3)), 4-(1-methylheptyloxycarbonyl)phenyl=3-fluoro-4-decanoyloxybenzoate (formula (1): m=9, $X^2=Y^1=Y^2=H$, $X^1=F$, n=6 (E4)), 2-fluoro-4-(1-methylheptyloxycarbonyl)phenyl=4-decanoyloxybenzoate (formula (1): m=9, $X^1=X^2=Y^2=H$, $Y^1=F$, n=6 (E5)), 2-fluoro-4-(1-methylheptyloxycarbonyl)phenyl=2-fluoro-4-decanoyloxybenzoate (formula (1): m=9, $X^1=Y^2=H$, $X^2=Y^1=F$, n=6 (E6)), and 2-fluoro-4-(1-methylheptyloxycarbonyl)phenyl=3-fluoro-4-decanoyloxybenzoate (formula (1): m=9, $X^1=Y^1=H$, $X^2=Y^2=F$, n=6 (E7))

End products were obtained in the same manner as in Example 1 except that p-hydroxybenzoic acid or 4-acetoxy benzoic acid which was substituted with fluorine on the benzene ring was used as required.

Table 1 shows 1H-NMR date of the end products obtained in Examples 1 to 7, and the chemical structures thereof are indicated by (E1) to (E7).

Comparative Example 1

Anti-ferroelectric liquid crystal compounds (2A, 2B) of the following formulae were mixed in a compound (2A)/compound (2B) mixing ratio of 70/30 (molar ratio) to obtain an anti-ferroelectric liquid crystal composition. Table 2 shows the phase sequence of the obtained composition.

2A: $C_9H_{19}O$—Ph—Ph—COO—Ph(3F)—COO—C*H($CF_3$)($CH_2$)$_5$O$C_2H_5$ (formula (2): R=$C_9H_{19}$, Z=F, A=$CF_3$, r=1, s=5, p=2)

2B: $C_8H_{17}O$—Ph—Ph—COO—Ph(3F)—COO—C*H($CH_3$)$C_5H_{11}$ (formula (2): R=$C_8H_{17}$, Z=F, A=$CH_3$, r=0, p=5)

Figure 4:
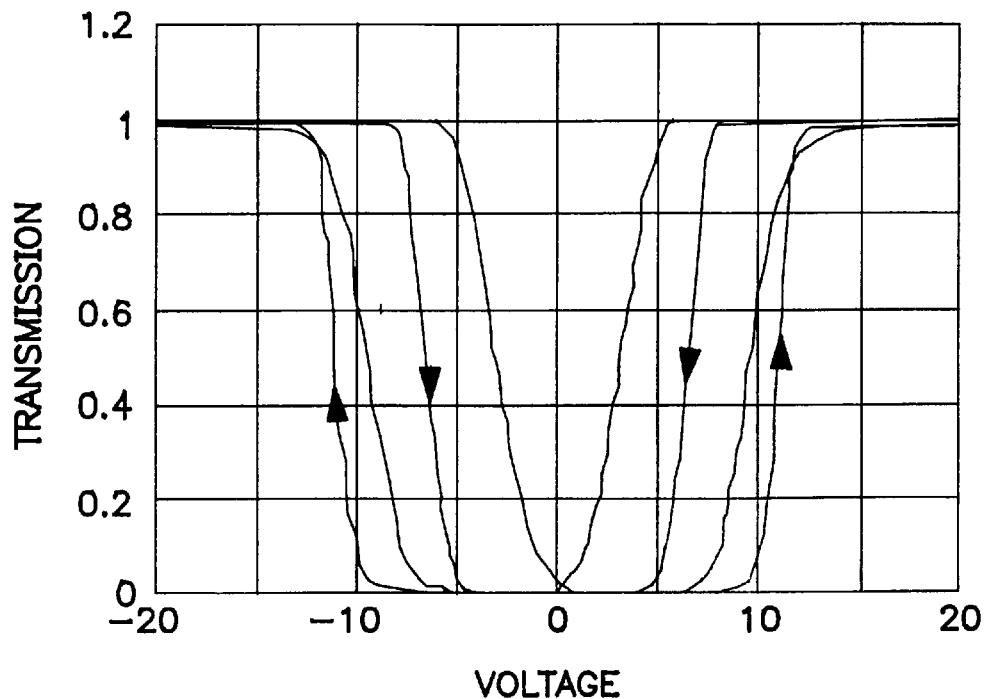
FIG. 4 shows optical responses in Comparative Examples 1 and 2, in which a hysteresis with arrows shows the optical response in Comparative Example 2 and a hysteresis with no arrow shows the optical response in Comparative Example 1.

When a triangular wave voltage was applied to the above anti-ferroelectric liquid crystal composition at 60° C., it had an optical hysteresis with regard to the applied voltage as shown in FIG. 4, and a large strain of hysteresis was observed. Further, the composition was measured for a spontaneous polarization at 60° C. and a response time in the transition from an anti-ferroelectric state to a ferroelectric state. Table 3 shows the results.

The above optical response hysteresis, response time and spontaneous polarization were measured as follows.

A liquid crystal cell (cell thickness 2 μm) having ITO electrodes and a rubbed polyimide thin film (30 nm) was charged with a liquid crystal composition in an isotropic state. Then, the cell was gradually cooled at a rate of 1.0° C./minute to align the liquid crystal. The cell was interposed between crossed polarizers such that the layer direction of the liquid crystal was in parallel with an analyzer or a polarizer. A ±30 V triangular wave voltage having a frequency of 30 mHz was applied to the cell, and the liquid crystal composition was measured for a change in transmittance with a photo-multiplier to obtain an optical response hysteresis.

The response time in a transition from an anti-ferroelectric state to a ferroelectric state was defined to be a time required for a change in transmittance from 10% to 90% when a maximum transmittance was 100%, and a (E₁)

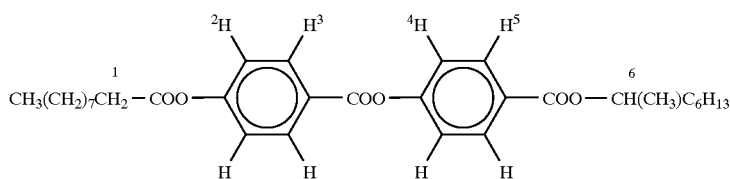

minimum transmittance was 0%, under the application of 30 V voltage having a frequency of 10 Hz was 100% at 60° C.

The spontaneous polarization was determined by applying a 25 V triangular wave at 60° C. and measuring a polarization inversion current.

Comparative Example 2

An optically active compound (3A) having the following formula was further mixed with the anti-ferroelectric liquid crystal compounds (2A, 2B) used in Comparative Example 1 in a 2A/2B/3A mixing ratio of 60/20/20 (molar ratio), and the composition was measured for a phase sequence, an optical response hysteresis, a spontaneous polarization and a response time in the same manner as in Comparative Example 1.

Tables 2 and 3 show the results.

3A: $C_9H_{19}$—COO—Ph—COO—Ph(3F)—COO—C*H($CH_3$)$C_6H_{13}$ (R-configuration)

TABLE 1

| Ex. No. & Symbols for compounds | Chemical shift | | | | | | | |
|---|---|---|---|---|---|---|---|---|
| | 1H | 2H | 3H | 4H | 5H | 6H | 7H | 8H |
| 1 (E1) | 2.6 | 7.3 | 8.1 | 7.3 | 8.2 | 5.2 | | |
| 2 (E2) | 2.6 | 7.3 | 8.1 | 7.3 | 8.2 | 5.2 | | |
| 3 (E3) | 2.6 | 7.0 | 7.0 | 8.2 | 7.3 | 8.2 | 5.2 | |
| 4 (E4) | 2.6 | 7.3 | 8.0 | 8.0 | 7.3 | 8.2 | 5.2 | |
| 5 (E5) | 2.6 | 7.2 | 8.3 | 7.4 | 7.9 | 7.9 | 5.2 | |
| 6 (E6) | 2.6 | 7.0 | 7.0 | 8.2 | 7.4 | 7.9 | 7.9 | 5.2 |
| 7 (E7) | 2.6 | 7.1 | 7.1 | 8.2 | 7.1 | 7.1 | 8.0 | 5.2 |

Ex. = Example

FIG. 4 shows the optical response hysteresis of the composition.

As shown in FIG. 4, the composition was improved in optical hysteresis by adding 3A, while the response speed was decreased.

Example 8

The racemic compound (E5) obtained in Example 5 was mixed with anti-ferroelectric liquid crystal compounds (2A, 2B) in a 2A/2B/E5 mixing ratio of 56/24/20 (molar ratio), and the composition was measured for a phase sequence, an optical response hysteresis, a spontaneous polarization and a response time in the same manner as in Comparative Example 1.

Tables 2 and 3 show the results.

Figure 5:
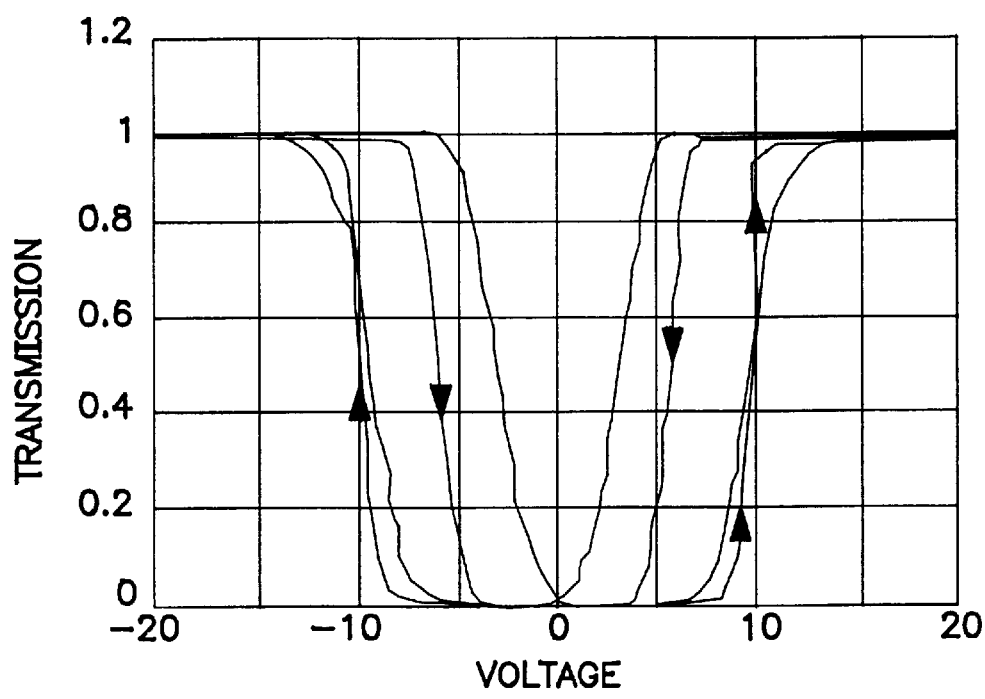
FIG. 5 shows optical responses in Comparative Examples 1 and Example 8, in which a hysteresis with arrows shows the optical response in Example 8 and a hysteresis with no arrow shows the optical response in Comparative Example 1.

Further, FIG. 5 shows the optical response hysteresis of the composition.

As shown in FIG. 5, the composition was improved in optical hysteresis and showed the performance of a high response speed, though its spontaneous polarization was about a half.

TABLE 2

| Ex. No. | Phase sequence |
|---|---|
| Ex. 8 | Cr(<−10)SCA*(73)SA(88)I |
| CEx. 1 | Cr(<−10)SCA*(95)SC*(97)SA(105)I |
| CEx. 2 | Cr(<−10)SCA*(74)SC*(75)SA(87)I |

Ex. = Example, CEx. = Comparative Example

In Table 2, parenthesized values show transition temperatures (unit: ° C.), Cr stands for a crystal phase, SCA* stands for an anti-ferroelectric phase, SC* stands for a ferroelectric phase, SA stands for a smectic A phase, and I stands for an isotropic phase.

TABLE 3

| Ex. No. | Spontaneous polarization (nC/cm$^2$) | Response time ($\mu$second) |
|---|---|---|
| Ex. 8 | 93 | 70 |
| CEx. 1 | 172 | 53 |
| CEx. 2 | 114 | 123 |

Ex. = Example, CEx. = Comparative Example

Examples 9–13

One of the racemic compounds (E1, E4, E3, E6 or E7) was mixed with an anti-ferroelectric liquid crystal composition which was a mixture of the anti-ferroelectric liquid crystal compounds (2A and 2B), in a 2A/2B/racemic compound mixing ratio of 56/24/20 (molar ratio), to obtain an anti-ferroelectric liquid crystal composition.

Example 14

Anti-ferroelectric liquid crystal compounds (2A and 2B) were mixed with the racemic compound (E5) in a 2A/2B/E5 mixing ratio of 49/21/30 (molar ratio), to obtain an anti-ferroelectric liquid crystal composition.

The anti-ferroelectric liquid crystal compositions obtained in Examples 9 to 14 were measured for a phase sequence, an optical response hysteresis, a spontaneous polarization and a response each. Tables 4 and 5 show the results.

The anti-ferroelectric liquid crystal compositions were measured for an optical response hysteresis with regard to an applied voltage when a triangular voltage was applied at 60° C. The composition obtained in Comparative Example 1 showed a large strain of hysteresis, while the compositions obtained in the above Examples showed a decreased steepness of threshold.

The spontaneous polarization was determined by measuring a polarization inversion current under the application of 25V triangular wave at 60° C.

TABLE 4

| Ex. No. (Racemic compound) | Phase sequence | Components | Molar ratio |
|---|---|---|---|
| Ex. 9 (E1) | Cr(<−20)SCA*(79)SC*(81)SA-(93)I | A2/B2/E1 = | 56/24/20 |
| Ex. 10 (E4) | Cr(<−20)SCA*(73)SA(89)I | A2/B2/E4 = | 56/24/20 |
| Ex. 11 (E3) | Cr(<−20)SCA*(76)SC*(77)SA-(82)I | A2/B2/E3 = | 56/24/20 |
| Ex. 12 (E6) | Cr(<−20)SCA*(66)SC*(69)SA-(86)I | A2/B2/E6 = | 56/24/20 |
| Ex. 13 (E7) | Cr(<−20)SCA*(74)SA(89)I | A2/B2/E7 = | 56/24/20 |
| Ex. 14 (E5) | Cr(<−20)SCA*(61)SA(78)I | A2/B2/E5 = | 49/21/30 |

Ex. = Example, CEx. = Comparative Example

In Table 4, parenthesized values show transition temperatures (unit: ° C.), Cr stands for a crystal phase, SCA* stands for an anti-ferroelectric phase, SC* stands for a ferroelectric phase, SA stands for a smectic A phase, and I stands for an isotropic phase.

TABLE 5

| Ex. No. (Racemic compound) | Spontaneous polarization (nC/cm$^2$) | Response time ($\mu$second) | Measurement temperature |
|---|---|---|---|
| Ex. 9 (E1) | 118 | 46 | 60° C. |
| Ex. 10 (E4) | 94 | 46 | 60° C. |
| Ex. 11 (E3) | 113 | 83 | 60° C. |
| Ex. 12 (E6) | 85 | 36 | 60° C. |
| Ex. 13 (E7) | 107 | 33 | 60° C. |
| Ex. 14 (E5) | 97 | 13 | 60° C. |

Ex. = Example, CEx. = Comparative Example

Example 15

Preparation of 3-fluoro-4-(1-methylbutyloxycarbonyl)phenyl=4-decanoyloxybenzoate (1) Preparation of 4-decanoyloxybenzoic acid 12.7 Grams (0.0917 mol) of p-hydroxybenzoic acid was added to 150 ml of dichloromethane, and 10.2 g (0.0917 mol) of triethylamine was added to the resultant suspension. The mixture was stirred until a uniform solution was formed. To the above solution was added 18.3 g (0.096 mol) of decanoyl chloride at such an appropriate rate at which dichloromethane was not refluxed. Then, 1.0 g (0.0085 mol) of 4-dimethylaminopyridine was added, and the mixture was stirred at room temperature overnight.

1N hydrochloric acid was added to the resultant reaction mixture, and the mixture was extracted with ether. The ether was distilled off, and the resultant crude product was washed with hexane and dried to give 19.4 g (yield 85%) of an intended carboxylic acid as an end product.

(2) Preparation of 4-acetoxy-2-fluoro-1-(1-methylbutyloxycarbonyl)benzene

Thionyl chloride in an amount of 60 ml was added to 10.8 g (0.06 mol) of 4-acetoxy-2-fluoro-benzoic acid, and the mixture was allowed to react under reflux for 7 hours. Then, excessive thionyl chloride was distilled off, and then 10 ml of pyridine and 3.5 g (0.0402 mol) of 2-pentanol were dropwise added.

After the dropwise addition, the mixture was stirred at room temperature for one day and night, and then the reaction mixture was diluted with 200 ml of ether. An organic layer was consecutively washed with a diluted hydrochloric acid, with a 1N sodium hydroxide aqueous solution and with water, and dried over magnesium sulfate. The solvent was distilled off, and the resultant crude end product was purified by silica gel column chromatography using hexane/ethyl acetate as solvents to give 10.8 g (yield 90%) of an end product.

(3) Preparation of 3-fluoro-4-hydroxy-1-(1-methylbutyloxycarbonyl)benzene 9.7 Grams (0.0361 mol) of the compound obtained in the above (2) was dissolved in 250 ml of ethanol, and 7.74 g (0.0772 mol) of benzylamine was dropwise added. Further, the mixture was stirred at room temperature for one day and night, then diluted with 300 ml of ether, consecutively washed with diluted hydrochloric acid and with water, and dried over magnesium sulfate. The solvent was distilled off, and then silica gel column chromatography was used for isolation and purification to give 8.0 g (yield 98%) of an end product.

(4) Preparation of 3-fluoro-4-(1-methylbutyloxycarbonyl)phenyl=4-n-decanoyloxybenzoate Thionyl chloride in an amount of 15 ml was added to 3.1 mmol of the compound obtained in the above (1), and the mixture was stirred under heating for 5 hours. Excessive thionyl chloride was distilled off, then, 2 ml of pyridine and 2.12 mmol of the compound obtained in the above (3) were added, and the mixture was allowed to react at room temperature for 10 hours. After termination of the reaction, the reaction mixture was diluted with 300 ml of ether and consecutively washed with diluted hydrochloric acid, with a 1N sodium carbonate aqueous solution and with water, and an organic layer was dried over magnesium sulfate. Then, the solvent was distilled off, and silica gel column chromatography was used for isolation to give 9.2 g (1.84 mmol, yield 87%) of an end product.

Examples 16–21

Example 16

Preparation of 3-fluoro-4-(1-methylhexyloxycarbonyl)phenyl=4-decanoyloxybenzoate (formula (1): m=9, n=5, $X^1=X^2=Y^1=H$, $Y^2=F$ (E9))

Example 17

Preparation of 3-fluoro-4-(1-methylnonyloxycarbonyl)phenyl=4-decanoyloxybenzoate (formula (1): m=9, n=8, $X^1=X^2=Y^1=H$, $Y^2=F$ (E10))

Example 18

Preparation of 3-fluoro-4-(1-methylheptyloxycarbonyl)phenyl=4-butanoyloxybenzoate (formula (1): m=3, n=6, $X^1=X^2=Y^1=H$, $Y^2=F$ (E11))

Example 19

Preparation of 3-fluoro-4-(1-methylheptyloxycarbonyl)phenyl=4-hexanoyloxybenzoate (formula (1): m=5, n=6, $X^1=X^2=Y^1=H$, $Y^2=F$ (E12))

Example 20

Preparation of 3-fluoro-4-(1-methylheptyloxycarbonyl)phenyl=4-octanoyloxybenzoate (formula (1): m=7, n=6, $X^1=X^2=Y^1=H$, $Y^2=F$ (E13))

Example 21

Preparation of 3-fluoro-4-(1-methylheptyloxycarbonyl)phenyl=4-undecanoyloxybenzoate (formula (1): m=10, n=6, $X^1=X^2=Y^1=H$, $Y^2=F$ (E14)).

Compounds in Examples 16 to 21 were obtained in the same manner as in Example 15.

Table 6 shows NMR data of the end products obtained in Examples 15 to 21, and the chemical structures thereof are indicated by (E8) to (E14).

TABLE 6

| Ex. No & | Chemical shift | | | | | | |
|---|---|---|---|---|---|---|---|
| Symbols | 1H | 2H | 3H | 4H | 5H | 6H | 7H |
| 15–21 (E8–E14) | 2.6 | 7.3 | 8.2 | 7.1 | 7.1 | 8.0 | 5.2 |

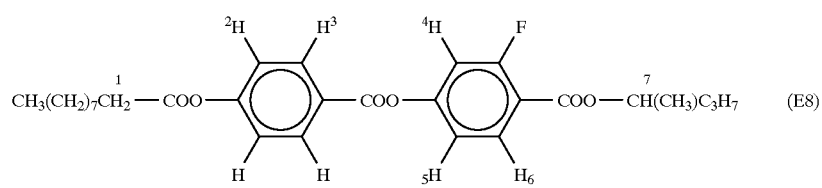

(E8)

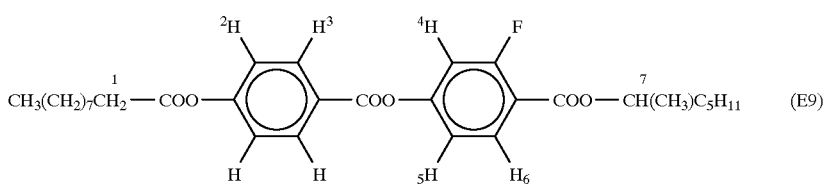

(E9)

TABLE 6-continued

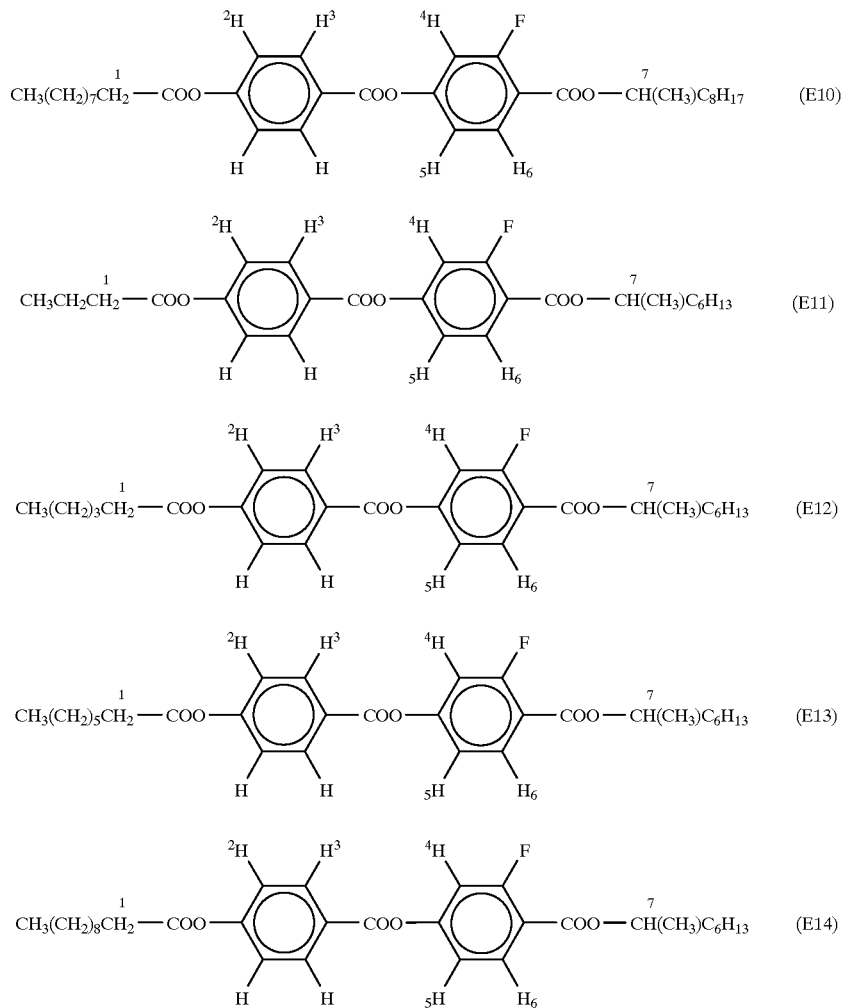

Ex. = Example

Examples 22–28

The racemic compounds (E8) to (E14) obtained in Examples 15 to 21 were respectively mixed with a composition containing the same anti-ferroelectric liquid crystal compounds (2A and 2B) as those used in Comparative Example 1, in a 2A/2B/racemic compound mixing ratio of 56/24/20 (molar ratio) to obtain an anti-ferroelectric liquid crystal composition.

The obtained compositions were measured for a phase sequence, an optical response hysteresis, a spontaneous polarization and a response time in the same manner as in Comparative Example 1. Table 7 shows the results together with the results of Comparative Example 1 as a reference.

All the compositions obtained in Examples 22 to 28 were improved in optical hysteresis, and showed the performance of a high response speed, though their spontaneous polarizations were decreased to a great extent.

TABLE 7

| Ex. No. (Racemic compound) | Phase sequence | Spontaneous polarization (nC/cm$^2$) | Response time (µsecond) |
|---|---|---|---|
| Ex. 22 (E8) | Cr(<−20)SCA*(79)SA(93)I | 122 | 42 |
| Ex. 23 (E9) | Cr(<−20)SCA*(76)SC*(78)SA-(90)I | 124 | 51 |
| Ex. 24 (E10) | Cr(<−20)SCA*(73)SC*(74)SA-(87)I | 115 | 47 |
| Ex. 25 (E11) | Cr(<−20)SCA*(73)SA(91)I | 95 | 35 |
| Ex. 26 (E12) | Cr(<−20)SCA*(75)SA(91)I | 107 | 48 |
| Ex. 27 (E13) | Cr(<−20)SCA*(76)SA(90)I | 111 | 39 |
| Ex. 28 (E14) | Cr(<−20)SCA*(74)SC*(77)SA-(90)I | 115 | 39 |
| CEx. 1 | Cr(<−20)SCA*(95)SC*(97)SA-(105)I | 172 | 53 |

Ex. = Example, CEx. = Comparative Example

In the phase sequence in Table 7, parenthesized values show transition temperatures (° C.), Cr stands for a crystal phase, SCA* stands for an anti-ferroelectric phase, SC* stands for a ferroelectric phase, SA stands for a smectic A phase, and I stands for an isotropic phase.

Example 29

The following compounds (i) to (iii) selected from the compounds of the formulae (1) and (2) in the present invention and the following compound (iv) were mixed to prepare a composition, and the composition was measured for a phase sequence, a response time, a tilt angle, a light leak in an anti-ferroelectric state and a steepness of threshold. Tables 8 and 9 show the results.

| Chemical formula | mol % |
| --- | --- |
| (i) $C_9H_{19}$—O—Ph—Ph—COO—Ph(3F)—COO—$C^*H(CF_3)(CH_2)_5OC_2H_5$ (2A) | 49 |
| (ii) $C_9H_{19}$—O—Ph—Ph—COO—Ph(3F)—COO—$C^*H(CH_3)C_5H_{11}$ | 21 |
| (iii) $C_9H_{19}$—COO—Ph—COO—Ph(3F)—COO—$CH(CH_3)C_6H_{13}$ (E2) | 15 |
| (iv) $C_9H_{19}$—COO—Ph—COO—Ph(3F)—COO—$C_7H_{15}$ | 15 |

In the above formulae, —Ph— stands for a 1,4-phenylene group, —Ph(3F)— stands for a 1,4-phenylene group containing fluorine substituted on the 3-position, and C* stands for an asymmetric carbon atom.

The phase sequence was determined by texture observation through a polarization microscope and DSC measurement. The response time, the tilt angle, the light leak and the steepness of threshold were determined as follows.

A liquid crystal cell (cell thickness 2 $\mu$m) having ITO electrodes and a rubbed polyimide thin film (30 nm) was charged with the composition in an isotropic state. Then, the cell was gradually cooled at a rate of 1.0° C./minute to align the liquid crystal. The cell was placed between crossed polarizers such that the layer direction of the liquid crystal was in parallel with an analyzer or a polarizer.

The response time (Response time I: in transition from an anti-ferroelectric state to a ferroelectric state) was defined to be a time required for a change in transmittance from 10% to 90% when a maximum transmittance was 100%, and a minimum transmittance was 0%, under the application of 30 V triangular wave voltage having a frequency of 10 Hz was 100% at 60° C.

The tilt angle was determined by applying ±30 V triangular voltage having a frequency of 30 Hz to the test cell at 30° C., rotating the test cell until a dark field was found and measuring the angle of the rotation.

The light leak (transmittance in an anti-ferroelectric state) was determined as follows.

The test cell was cooled to 30° C., and ±30 V square wave voltage having a frequency of 30 Hz was applied for 5 minutes to decrease a zigzag defect. Further, the amount of light transmitted through the cell was detected with a photo-multiplier, and the test cell was rotated such that the amounts of transmitted light in both anti-ferroelectric states generated in switching were equivalent.

After the application of voltage, the amount of transmitted light in an anti-ferroelectric state was measured with a photo-multiplier. Further, 30 V direct current was applied to the cell to bring the composition into a ferroelectric state, and the amount of transmitted light in this state was measured with a photo-multiplier.

Then, an empty cell was placed between the crossed polarizers, and the amount of transmitted light was similarly measured.

The above amount of transmitted light was taken as a light leak by polarization plates. The amount of transmitted light in a ferroelectric state was taken as 100%, the amount of transmitted light with the empty cell was taken as 0%, and the transmittance (light leak) in an anti-ferroelectric state was calculated.

In a hysteresis curve in a change from an anti-ferroelectric state to a ferroelectric state when ±30 V triangular wave voltage having a frequency of 30 Hz was applied to the test cell, the steepness of threshold was defined as follows.

Steepness of threshold=$(0.9-0.1)/(V_{90}-V_{10})$ (unit; 1/V)

$V_{90}$=voltage in transmittance of 90%

$V_{10}$=voltage in transmittance of 10%

The greater the value obtained by the calculation on the basis of the above equation is, the better the steepness of threshold of a liquid crystal.

Example 30

The following compounds (i) to (iii) selected from the compounds of the formulae (1) and (2) in the present invention and the following compound (iv) were mixed to prepare a composition, and the composition was measured for a phase sequence, a response time, a tilt angle, a light leak in an anti-ferroelectric state and a steepness of threshold. Tables 8 and 9 show the results.

| Chemical formula | mol % |
| --- | --- |
| (i) $C_9H_{19}$—O—Ph—Ph—COO—Ph(3F)—COO—$C^*H(CF_3)(CH_2)_5OC_2H_5$ (2A) | 52.5 |
| (ii) $C_8H_{17}$—O—Ph—Ph—COO—Ph(3F)—COO—$C^*H(CH_3)C_5H_{11}$ (2B) | 22.5 |
| (iii) $C_9H_{19}$—COO—Ph—COO—Ph(3F)—COO—$CH(CH_3)C_6H_{13}$ (E2) | 15 |
| (iv) $C_9H_{19}$—COO—Ph—COO—Ph(3F)—COO—$C_7H_{15}$ | 10 |

In the above formulae, —Ph—, —Ph(3F)— and C* are as defined in Example 29.

Comparative Example 3

The following compounds (i) and (ii) selected from the compound of the formula (2) in the present invention were mixed to prepare a composition, and the composition was measured for a phase sequence, a response time, a tilt angle, a light leak in an anti-ferroelectric state and a steepness of threshold. Tables 8 and 9 show the results.

TABLE 8

| | Phase sequence |
|---|---|
| Example 29 | Cr(<−20)SCA*(71)SC*(73)SA(88)I |
| Example 30 | Cr(<−20)SCA*(72)SC*(76)SA(90)I |
| Comparative Example 3 | Cr(<−10)SCA*(58)SC*(101)SA(111)I |

In the above formulae, —Ph—, —Ph(3F)— and C* are as defined in Example 29.

TABLE 9

| Ex. No. | Response time ($\mu$second) | Tilt angle (°) | Light leak (%) | Steepness of threshold (1/V) |
|---|---|---|---|---|
| Ex. 29 | 35 | 30 | 1.6 | 0.7 |
| Ex. 30 | 40 | 31 | 1.0 | 0.8 |
| CEx. 3 | 106 | 35 | 1.5 | 0.3 |

In the phase sequences, parenthesized values show transition temperatures (° C.), Cr stands for a crystal phase, SCA* stands for an anti-ferroelectric phase, SC* stands for a ferroelectric phase, SA stands for a smectic A phase, and I stands for an isotropic phase.

In the above formulae, —Ph— is a 1,4-phenylene group, —Ph(3F) is a 1,4-phenylene group containing fluorine substituted on the 3-position, and C* is an asymmetric carbon atom.

Example 32

The following compounds (i) to (iii) were selected from the compounds of the formulae (1) and (2) in the present invention and mixed to prepare a composition, and the composition was measured for a phase sequence, a response time, a tilt angle and a light leak in an anti-ferroelectric state. Tables 10 and 11 show the results.

TABLE 10

| Ex. No. | Phase sequence |
|---|---|
| Example 31 | Cr(<−20)SCA*(77)SC*(79)SA(84) |
| Example 32 | Cr(<−20)SCA*(72)SA(81)I |
| Example 33 | Cr(<−20)SCA*(81)SA(88)I |

In the above formulae, —Ph—, —Ph(3F)— and C* are as defined in Example 31.

Example 33

The following compounds (i) to (iii) were selected from the compounds of the formulae (1) and (2) in the present invention and mixed to prepare a composition, and the composition was measured for a phase sequence, a response time, a tilt angle and a light leak in an anti-ferroelectric state. Tables 10 and 11 show the results.

| Chemical formula | mol % |
|---|---|
| (i) $C_9H_{19}$—O—Ph—Ph—COO—Ph(3F)—COO—C*H($CF_3$)($CH_2$)$_5$O$C_2H_5$ (2A) | 60.0 |
| (ii) $C_8H_{17}$—O—Ph—Ph—COO—Ph(3F)—COO—C*H($CH_3$)$C_5H_{11}$ (2B) | 40.0 |

Example 31

The following compounds (i) to (iii) were selected from the compounds of the formulae (1) and (2) in the present invention and mixed to prepare a composition, and the composition was measured for a phase sequence, a response time, a tilt angle and a light leak in an anti-ferroelectric state. Tables 10 and 11 show the results.

| Chemical formula | mol % |
|---|---|
| (i) $C_9H_{19}$—O—Ph—Ph—COO—Ph(3F)—COO—C*H($CF_3$)($CH_2$)$_5$O$C_2H_5$ (2A) | 80 |
| (ii) $C_9H_{19}$—O—Ph—Ph—COO—Ph(3F)—COO—C*H($CH_3$)$C_5H_{11}$ | 10 |
| (iii) $C_9H_{19}$—COO—Ph—COO—Ph(3F)—COO—CH($CH_3$)$C_5H_{11}$ (E9) | 10 |

| Chemical formula | mol % |
|---|---|
| (i) $C_8H_{17}$—O—Ph—Ph—COO—Ph(3F)—COO—C*H($CF_3$)($CH_2$)$_5$O$C_2H_5$ | 74 |
| (ii) $C_9H_{19}$—O—Ph—Ph—COO—Ph(3F)—COO—C*H($CH_3$)$C_5H_{11}$ | 10 |
| (iii) $C_9H_{19}$—COO—Ph—COO—Ph(3F)—COO—CH($CH_3$)$C_5H_{11}$ (E9) | 16 |

In the above formulae, —Ph—, —Ph(3F)— and C* are as defined in Example 31.

TABLE 10

| Ex. No. | Phase sequence |
|---|---|
| Example 31 | Cr(<−20)SCA*(77)SC*(79)SA(84) |
| Example 32 | Cr(<−20)SCA*(72)SA(81)I |
| Example 33 | Cr(<−20)SCA*(81)SA(88)I |

TABLE 11

| Ex. No. | Response time (μsecond) | Tilt angle (°) | Light leak (%) |
|---|---|---|---|
| Example 31 | 31 | 35 | 1.2 |
| Example 32 | 35 | 34 | 1.6 |
| Example 33 | 29 | 34 | 0.7 |

Example 34

The following compounds (i) to (iii) were selected from the compounds of the formulae (1) and (2) in the present invention and mixed with the following compound (iv) to prepare a composition, and the composition was measured for a phase sequence, a response time, a tilt angle, a light leak in an anti-ferroelectric state and a steepness of threshold. Tables 11 and 12 show the results.

| Chemical formula | mol % |
|---|---|
| (i) $C_9H_{19}$—O—Ph—Ph—COO—Ph(3F)—COO—C*H($CF_3$)($CH_2$)$_5$O$C_2H_5$ (2A) | 37.5 |
| (ii) $C_9H_{19}$—O—Ph—Ph—COO—Ph(3F)—COO—C*H($CH_3$)$C_5H_{11}$ | 22.5 |
| (iii) $C_9H_{19}$—COO—Ph(3F)—COO—Ph(3F)—COO—CH($CH_3$)$C_5H_{11}$ | 30 |
| (iv) $C_9H_{19}$—COO—Ph—COO—Ph(3F)—COO—($CH_2$)$_7CH_3$ | 10 |

Example 35

A composition was prepared from the same compounds as those in Example 34 except that the compound (iv) was replaced with the following compound (iv-B).
(iv-B) $C_9H_{19}$—COO—Ph—COO—Ph(3F)—COO—($CH_2$)$_5CH_3$ The composition was measured for a phase sequence, a response time, a tilt angle, a light leak in an anti-ferroelectric state and a steepness of threshold. Tables 12 and 13 show the results.

Example 36

A composition was prepared from the same compounds as those in Example 34 except that the compound (iii) was replaced with the following compound (iii-B).
(iii-B) $C_7H_{15}$—COO—Ph(3F)—COO—Ph(3F)—COO—CH($CH_3$)$C_5H_{11}$ The composition was measured for a phase sequence, a response time, a tilt angle, a light leak in an anti-ferroelectric state and a steepness of threshold. Tables 12 and 13 show the results.

TABLE 12

| Ex. No. | Phase sequence |
|---|---|
| Example 34 | Cr(<−20)SCA*(64)SA(84)I |
| Example 35 | Cr(<−20)SCA*(60)SA(80)I |
| Example 36 | Cr(<−20)SCA*(61)SA(81)I |

TABLE 13

| Ex. No. | Response time (μsecond) | Tilt angle (°) | Light leak (%) | Steepness of threshold ($V^{-1}$) |
|---|---|---|---|---|
| Example 34 | 40 | 27 | 0.8 | 0.8 |
| Example 35 | 45 | 25 | 1.2 | 0.8 |
| Example 36 | 45 | 25 | 1.2 | 0.9 |

What is claimed is:

1. An anti-ferroelectric liquid crystal composition consisting essentially of a racemic compound of the formula (1),

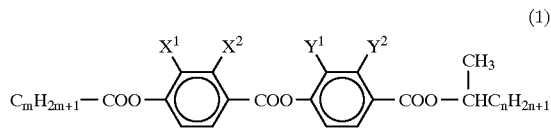

wherein m is an integer of 3 to 12, n is an integer of 3 to 8, each of $X^1$ and $X^2$ is a hydrogen atom together or one is a hydrogen atom and the other is a fluorine atom, and each of $Y^1$ and $Y^2$ is a hydrogen atom together or one is a hydrogen atom and the other is a fluorine atom, and an anti-ferroelectric liquid crystal compound of the following formula (2),

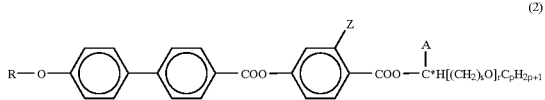
(2)

wherein R is a linear alkyl group having 6 to 12 carbon atoms, Z is a hydrogen atom or a fluorine atom, A is —$CH_3$ or —$CF_3$, and r is 0 or 1, provided that when A is —$CH_3$, r is 0 and p is an integer of 4 to 10, that when A is —$CF_3$ and r is 0, p is an integer of 6 to 8, and that when A is —$CF_3$ and r is 1, s is an integer of 5 to 8, p is an integer of 2 or 4 and C* is an asymmetric carbon atom.

2. The anti-ferroelectric liquid crystal composition of claim 1, wherein the composition contains the compound of the formula (1) in which m is 9.

3. The anti-ferroelectric liquid crystal composition of any one of claims 1 or 2, wherein the composition contains the compound of the formula (1) in which each of $X^1$, $X^2$ and $Y^1$ is a hydrogen atom together and $Y^2$ is a fluorine atom.

4. The anti-ferroelectric liquid crystal composition of any one of claims 1 or 2, wherein the composition contains the compound of the formula (2) in which A is —$CF_3$, r is 1, s is an integer of 5 to 8 and p is 2 or 4.

5. The anti-ferroelectric liquid crystal composition of any one of claims 1 or 2, wherein the composition contains the compound of the formula (2) in which A is —$CH_3$, r is 0 and p is an integer of 4 to 6.

6. The anti-ferroelectric liquid crystal composition of claim 1, wherein the composition contains a racemic compound of the formula (1) and the anti-ferroelectric liquid crystal compound of the formula (2) in a proportion of from 1:99 to 60:40 in terms of a molar ratio.

7. The anti-ferroelectric liquid crystal composition of claim 1, wherein at least a smectic A phase is present on a higher temperature side than an anti-ferroelectric phase and the anti-ferroelectric phase has an upper limit temperature of at least 40° C. and a lower limit temperature of 0° C. or lower.

8. The anti-ferroelectric liquid crystal composition of claim 1, wherein at least 2 compounds selected from anti-ferroelectric liquid crystal compounds of the formula (2) are used in admixture.

9. An anti-ferroelectric liquid crystal display device formed by interposing the anti-ferroelectric liquid crystal composition of claim 1 between a pair of electrode substrates.

10. The anti-ferroelectric liquid crystal composition of claim 3, wherein the composition contains the compound of formula (2) in which A is —$CF_3$, r is 1, s is an integer of 5 to 8, and p is 2 or 4.

11. The anti-ferroelectric liquid crystal composition of claim 3, wherein the composition contains the compound of the formula (2) in which A is —$CH_3$, r is 0 and p is an integer of 4 to 6.

* * * * *